United States Patent
Doering

(10) Patent No.: US 9,399,006 B2
(45) Date of Patent: Jul. 26, 2016

(54) ANTIPERSPIRANT WITH ANHYDROUS COMPOSITIONS

(71) Applicant: Henkel AG & Co. KGaA, Duesseldorf (DE)

(72) Inventor: Thomas Doering, Dormagen (DE)

(73) Assignee: Henkel AG & Co. KGaA, Duesseldorf (DE)

(*) Notice: Subject to any disclaimer, the term of this patent is extended or adjusted under 35 U.S.C. 154(b) by 245 days.

(21) Appl. No.: 14/104,437

(22) Filed: Dec. 12, 2013

(65) Prior Publication Data
US 2014/0169856 A1    Jun. 19, 2014

(30) Foreign Application Priority Data
Dec. 14, 2012 (DE) .......................... 10 2012 223 197

(51) Int. Cl.
| | |
|---|---|
| *B43K 5/06* | (2006.01) |
| *A61K 8/34* | (2006.01) |
| *A45D 40/00* | (2006.01) |
| *A61K 8/19* | (2006.01) |
| *A61K 8/26* | (2006.01) |
| *A61K 8/28* | (2006.01) |
| *A61K 8/89* | (2006.01) |
| *A61K 8/92* | (2006.01) |
| *A61Q 15/00* | (2006.01) |
| *A61K 8/31* | (2006.01) |
| *A61K 8/58* | (2006.01) |
| *A61K 8/891* | (2006.01) |

(52) U.S. Cl.
CPC ................ *A61K 8/342* (2013.01); *A45D 40/00* (2013.01); *A61K 8/19* (2013.01); *A61K 8/26* (2013.01); *A61K 8/28* (2013.01); *A61K 8/31* (2013.01); *A61K 8/585* (2013.01); *A61K 8/89* (2013.01); *A61K 8/891* (2013.01); *A61K 8/92* (2013.01); *A61Q 15/00* (2013.01); *A61K 2800/31* (2013.01); *A61K 2800/87* (2013.01)

(58) Field of Classification Search
CPC ........... A61K 8/342; A61K 8/26; A61K 8/28; A45D 40/06; A45D 40/065
USPC ........................................ 424/66–68; 401/68
See application file for complete search history.

(56) References Cited

U.S. PATENT DOCUMENTS

| | | | |
|---|---|---|---|
| 2,571,030 A | 10/1951 | Govett et al. | |
| 4,017,599 A | 4/1977 | Rubino | |
| 4,775,528 A | 10/1988 | Callaghan et al. | |
| 5,643,558 A | 7/1997 | Provancal et al. | |
| 6,010,688 A | 1/2000 | Shen | |
| 6,042,816 A | 3/2000 | Shen | |
| 6,245,325 B1 | 6/2001 | Shen | |
| 6,435,748 B1 * | 8/2002 | Taghikhani | A45D 40/04 401/175 |
| 6,436,381 B1 | 8/2002 | Carrillo et al. | |
| 6,649,152 B2 | 11/2003 | Carrillo et al. | |
| 6,663,854 B1 | 12/2003 | Shen et al. | |
| 6,902,723 B2 | 6/2005 | Shen | |
| 6,923,952 B2 | 8/2005 | Allen et al. | |
| 7,105,691 B2 | 9/2006 | Holerca et al. | |
| 8,518,385 B2 * | 8/2013 | Dierker | A61K 8/0229 424/66 |
| 2004/0009133 A1 | 1/2004 | Kolodzik et al. | |
| 2008/0267895 A1 * | 10/2008 | Franklin | A61K 8/26 424/68 |
| 2012/0009232 A1 * | 1/2012 | Yarlagadda | 424/401 |

FOREIGN PATENT DOCUMENTS

| | | | | |
|---|---|---|---|---|
| DE | 19756454 C1 | 6/1999 | | |
| DE | 10333245 A1 | 7/2005 | | |
| DE | 102004011968 A1 | 9/2005 | | |
| ES | WO 2012076177 A2 * | 6/2012 | ............ | A61K 8/342 |
| GB | 2048229 A | 12/1980 | | |
| GB | 2299506 A | 10/1996 | | |

* cited by examiner

*Primary Examiner* — Jennifer C Chiang
(74) *Attorney, Agent, or Firm* — P. Scott Smith

(57) ABSTRACT

Anhydrous soft slid antiperspirant compositions include, relative in each case to the total weight of the composition,
   at least one antiperspirant active ingredient,
   at least one oil in a total amount from 20 to 80 wt. %,
   at least one fatty alcohol having 12 to 18 carbon atoms,
   at least one fatty alcohol having more than 18 carbon atoms, with the proviso that
   the total amount of fatty alcohols is 3 to 12 wt. %,
   the weight ratio of fatty alcohols having 12 to 18 carbon atoms to the other fatty alcohols is in a weight ratio range from 1:1 to 1:3.

20 Claims, No Drawings

ANTIPERSPIRANT WITH ANHYDROUS COMPOSITIONS

FIELD OF THE INVENTION

The present invention generally relates to cosmetics to prevent body odor, in particular anhydrous compositions, which are applied as a non-aerosol.

BACKGROUND OF THE INVENTION

Compositions to prevent body odor are an important element of daily personal hygiene. They are designed to ensure that sweat formed during the course of the day through various activities (physical movement, work, sport) but also through psychological stress do not lead to unpleasant body odor. The deodorizing active ingredients contained in commercial deodorants are just as diverse as the constituents of sweat and the causes of the development of body odor. Odor absorbers, scents, deodorizing ion-exchangers, bacteriostatic agents, components having a prebiotic effect and enzyme inhibitors can be used as cosmetic deodorizing active ingredients. In simplified terms, body odor is attributable to the bacterial decomposition of the organic constituents of sweat. In turn, some of the bacteria that are typical of the natural microflora of human skin, in particular gram-positive anaerobic cocci, for example Staphylococci, such as *Staphylococcus hominis*, and *Corynebacteria*, are responsible for the bacterial decomposition. As body odor is caused by bacterial activity, it can be prevented particularly effectively by the application of cosmetic agents (soaps, creams, powders, sticks, roll-ons, gels or sprays) containing antimicrobially active substances and perfume oil compositions. Triclosan and chlorhexidine are among the antimicrobially active substances used to produce deodorants. Moreover, essential oils such as clove oil (eugenol), peppermint oil (menthol) and thyme oil (thymol) are used as active ingredients for deodorants, although the pronounced inherent odor of these compounds limits the dose in which they are used. From an ecological perspective triclosan, as an organic chlorine compound, is not without controversy. Essential oils have a relatively high allergenic potential, and this, in addition to their inherent odor, restricts their usage. Aromatic alcohols, such as for example 2-methyl-5-phenylpentan-1-ol, 2-phenylethan-1-ol or 3-phenylpropan-1-ol, are already known in the prior art as antimicrobial and deodorizing active ingredients. These compounds are highly effective, are also very well tolerated by the skin, and have only a weak inherent odor.

The aerosol spray, roll-on and antiperspirant stick have become established in the market as application forms for said compositions. Furthermore, deodorants in powder form (including compressed powders) or deodorants applied to a disposable substrate (such as a cloth, pad or swab) are also known. "Soft solids" are known to the person skilled in the art as a particularly pleasant application form. These are viscous compositions which have a creamy texture and which are pressed out through one or more openings of a dispensing device of the applicator before use. This process exerts a pressure on the composition, under which the formulation often becomes unstable, causing one of its liquid constituents to separate out. This phenomenon is known as syneresis and is mostly to be observed in soft solids with a high oil content.

It is therefore desirable to provide a deodorizing cosmetic composition in the form of an anhydrous composition as a soft solid, which exhibits no or at least reduced syneresis. The composition should moreover impart a light, powdery and dry feel to the skin. When the composition comes into contact with textiles, the composition should wash easily out of the textiles.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An anhydrous composition including, relative in each case to the total weight of the composition, at least one antiperspirant active ingredient, at least one oil in a total amount from 20 to 80 wt. %, at least one fatty alcohol having 12 to 18 carbon atoms, at least one fatty alcohol having more than 18 carbon atoms, with the proviso that the total amount of fatty alcohols is 3 to 12 wt. %, the weight ratio of fatty alcohols having 12 to 18 carbon atoms to the other fatty alcohols is in a weight ratio range from 1:1 to 1:3.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It was found that the above objects and others are met by an anhydrous compositions containing, relative in each case to the total weight of the composition,
  at least one antiperspirant active ingredient,
  at least one oil in a total amount from 20 to 80 wt. %,
  at least one (in particular solid) fatty alcohol having 12 to 18 carbon atoms,
  at least one (in particular solid) fatty alcohol having more than 18 carbon atoms, with the proviso that
  the total amount of (in particular solid) fatty alcohols is 3 to 12 wt. %,
  the weight ratio of (in particular solid) fatty alcohols having 12 to 18 carbon atoms to the other (in particular solid) fatty alcohols is in a weight ratio range from 1:1 to 1:3.

Fatty alcohols are understood according to the invention to be primary alcohols in the form of monohydroxyl compounds of a linear, aliphatic hydrocarbon, wherein said hydrocarbon has at least 12 carbon atoms and bears no further substituents apart from the hydroxyl group.

All details of the states of aggregation of the starting substances that are used (solid, liquid, etc.) in this application relate to normal conditions. "Normal conditions" within the meaning of the present application are a temperature of 20° C. and a pressure of 1013.25 mbar. Melting point details likewise relate to a pressure of 1013.25 mbar.

The term "anhydrous" is understood according to the invention to mean that the compositions contain 0 to a maximum of 3 wt. %, preferably 0 to a maximum of 2 wt. %, of free water, relative to the total composition. The content of water of crystallization, water of hydration or similarly molecularly bound water that may be contained in the constituents used, in particular in sweat-inhibiting active ingredients that are optionally included, do not constitute free water within the meaning of the present application.

The compositions according to the invention must include at least one sweat-inhibiting active ingredient, also referred to as an antiperspirant active ingredient, to support the overall deodorant performance of the product.

More preferred compositions according to the invention are characterized in that the at least one antiperspirant active ingredient is included in an amount from 3 to 35 wt. %, preferably 5 to 30 wt. % and more preferably 10 to 23 wt. %, relative to the total weight of active substance (USP) free from water of crystallization in the total composition.

Preferred antiperspirant active ingredients are selected from the water-soluble astringent inorganic and organic salts of aluminum, zirconium and zinc and any mixtures of these salts.

According to the invention water solubility is understood to mean a solubility of at least 5 wt. % at 20° C., in other words amounts of at least 5 g of the antiperspirant active ingredient are soluble in 95 g of water at 20° C.

More preferred antiperspirant active ingredients are selected from aluminum chlorohydrate, in particular aluminum chlorohydrate of the general formula $[Al_2(OH)_5Cl.1\text{-}6\,H_2O]_n$, preferably $[Al_2(OH)_5Cl.2.3\,H_2O]_n$, which can be present in non-activated or in activated (depolymerized) form, and aluminum chlorohydrate of the general formula $[Al_2(OH)_4Cl_2.1\text{-}6\,H_2O]_n$, preferably $[Al_2(OH)_4Cl_2.2\text{-}3\,H_2O]_n$, which can be present in non-activated or in activated (depolymerized) form.

The production of preferred antiperspirant active ingredients is disclosed for example in U.S. Pat. No. 3,887,692, U.S. Pat. No. 3,904,741, U.S. Pat. No. 4,359,456, GB 2048229 and GB 1347950.

Also preferred are aluminum sesquichlorohydrate, aluminum dichlorohydrate, aluminum chlorohydrex propylene glycol (PG) or aluminum chlorohydrex polyethylene glycol (PEG), aluminum or aluminum zirconium glycol complexes, e.g. aluminum or aluminum zirconium propylene glycol complexes, aluminum sesquichlorohydrex PG or aluminum sesquichlorohydrex PEG, aluminum PG dichlorohydrex or aluminum PEG dichlorohydrex, aluminum hydroxide, selected furthermore from aluminum zirconium chlorohydrates, such as aluminum zirconium trichlorohydrate, aluminum zirconium tetrachlorohydrate, aluminum zirconium pentachlorohydrate, aluminum zirconium octachlorohydrate, aluminum zirconium chlorohydrate glycine complexes such as aluminum zirconium trichlorohydrex glycine, aluminum zirconium tetrachlorohydrex glycine, aluminum zirconium pentachlorohydrex glycine, aluminum zirconium octachlorohydrex glycine, potassium aluminum sulfate $(KAl(SO_4)_2.12\,H_2O$, alum), aluminum undecylenoyl collagen amino acid, sodium aluminum lactate+aluminum sulfate, sodium aluminum chlorohydroxylactate, aluminum bromohydrate, aluminum chloride, complexes of zinc and sodium salts, complexes of lanthanum and cerium, aluminum salts of lipoamino acids, aluminum sulfate, aluminum lactate, aluminum chlorohydroxyallantoinate, sodium aluminum chlorohydroxylactate, zinc chloride, zinc sulfocarbolate, zinc sulfate, zirconyl oxyhalides, in particular zirconyl oxychlorides, zirconyl hydroxyhalides, in particular zirconyl hydroxychlorides (zirconium chlorohydrate).

Antiperspirant active ingredients that are more preferred according to the invention are selected from "activated" aluminum and aluminum zirconium salts, which are also described as antiperspirant active ingredients with enhanced activity. Such active ingredients are known in the prior art and are also available commercially. Their production is disclosed in GB 2048229, U.S. Pat. No. 4,775,528 and U.S. Pat. No. 6,010,688, for example. Activated aluminum and aluminum zirconium salts are generally produced by heat treating a relatively dilute solution of the salt (e.g. approximately 10 wt. % salt) to increase its HPLC peak 4 to peak 3 surface area ratio. The activated salt can then be dried, in particular spray-dried, to form a powder. In addition to spray drying, drum drying for example is also suitable.

Activated aluminum and aluminum zirconium salts typically have an HPLC peak 4 to peak 3 surface area ratio of at least 0.4, preferably at least 0.7, more preferably at least 0.9, wherein at least 70% of the aluminum can be assigned to these peaks.

Activated aluminum and aluminum zirconium salts do not necessarily have to be used as a spray-dried powder. Sweat-inhibiting active ingredients that are likewise preferred according to the invention are non-aqueous solutions or solubilizates of an activated sweat-inhibiting aluminum or aluminum zirconium salt, for example according to U.S. Pat. No. 6,010,688, which are stabilized against loss of activation by the rapid degradation of the HPLC peak 4 to peak 3 surface area ratio of the salt by the addition of an effective amount of a polyhydric alcohol having 3 to 6 carbon atoms and 3 to 6 hydroxyl groups, preferably propylene glycol, sorbitol and pentaerythritol. Compositions are preferred for example that include in percent by weight (USP): 18 to 45 wt. % of an activated aluminum or aluminum zirconium salt, 55 to 82 wt. % of at least one anhydrous polyhydric alcohol having 3 to 6 carbon atoms and 3 to 6 hydroxyl groups, preferably propylene glycol, butylene glycol, diethylene glycol, dipropylene glycol, glycerol, sorbitol and pentaerythritol, more preferably propylene glycol.

Complexes of activated sweat-inhibiting aluminum or aluminum zirconium salts with a polyhydric alcohol including 20 to 50 wt. %, more preferably 20 to 42 wt. %, of activated sweat-inhibiting aluminum or aluminum zirconium salt and 2 to 16 wt. % of molecularly bound water are also more preferred, wherein the remainder up to 100 wt. % is made up by at least one polyhydric alcohol having 3 to 6 carbon atoms and 3 to 6 hydroxyl groups. Propylene glycol, propylene glycol/sorbitol mixtures and propylene glycol/pentaerythritol mixtures are preferred alcohols of this type. Such complexes of an activated sweat-inhibiting aluminum or aluminum zirconium salt with a polyhydric alcohol that are preferred according to the invention are disclosed in U.S. Pat. No. 5,643,558 and U.S. Pat. No. 6,245,325 for example.

Further preferred sweat-inhibiting active ingredients are basic calcium aluminum salts such as are disclosed in U.S. Pat. No. 2,571,030 for example. These salts are produced by reacting calcium carbonate with aluminum chlorohydroxide or aluminum chloride and aluminum powder or by adding calcium chloride dihydrate to aluminum chlorohydroxide.

Further preferred sweat-inhibiting active ingredients are aluminum zirconium complexes such as are disclosed in U.S. Pat. No. 4,017,599 for example, which are buffered with salts of amino acids, in particular with alkali and alkaline-earth glycinates.

Further preferred sweat-inhibiting active ingredients are activated aluminum or aluminum zirconium salts, such as are disclosed in U.S. Pat. No. 6,245,325 or U.S. Pat. No. 6,042,816 for example, including 5 to 78 wt. % (USP) of an activated sweat-inhibiting aluminum or aluminum zirconium salt, an amino acid or hydroxyalkanoic acid in an amount to provide a weight ratio of (amino acid or hydroxyalkanoic acid) to (Al+Zr) of 2:1 to 1:20 and preferably 1:1 to 1:10, and a water-soluble calcium salt in an amount to provide a weight ratio of Ca to (Al+Zr) of 1:1 to 1:28 and preferably 1:2 to 1:25. More preferred solid activated sweat-inhibiting salt compositions, according to U.S. Pat. No. 6,245,325 or U.S. Pat. No. 6,042,816 for example, include 48 to 78 wt. % (USP), preferably 66 to 75 wt. % of an activated aluminum or aluminum zirconium salt and 1 to 16 wt. %, preferably 4 to 13 wt. % of molecularly bound water (water of hydration), also sufficient water-soluble calcium salt that the weight ratio of Ca to (Al+Zr) is 1:1 to 1:28, preferably 1:2 to 1:25, and sufficient amino acid that the weight ratio of amino acid to (Al+Zr) is 2:1 to 1:20, preferably 1:1 to 1:10.

Further more preferred solid sweat-inhibiting activated salt compositions, according to U.S. Pat. No. 6,245,325 or U.S. Pat. No. 6,042,816 for example, include 48 to 78 wt. % (USP), preferably 66 to 75 wt. % of an activated aluminum or aluminum zirconium salt and 1 to 16 wt. %, preferably 4 to 13 wt. % of molecularly bound water (water of hydration), also sufficient water-soluble calcium salt that the weight ratio of Ca to (Al+Zr) is 1:1 to 1:28, preferably 1:2 to 1:25, and sufficient glycine that the weight ratio of glycine to (Al+Zr) is 2:1 to 1:20, preferably 1:1 to 1:10.

Further more preferred solid sweat-inhibiting activated salt compositions, according to U.S. Pat. No. 6,245,325 or U.S. Pat. No. 6,042,816 for example, include 48 to 78 wt. % (USP), preferably 66 to 75 wt. % of an activated aluminum or aluminum zirconium salt and 1 to 16 wt. %, preferably 4 to 13 wt. % of molecularly bound water, also sufficient water-soluble calcium salt that the weight ratio of Ca to (Al+Zr) is 1:1 to 1:28, preferably 1:2 to 1:25, and sufficient hydroxyalkanoic acid that the weight ratio of hydroxyalkanoic acid to (Al+Zr) is 2:1 to 1:20, preferably 1:1 to 1:10.

Preferred water-soluble calcium salts for stabilizing the sweat-inhibiting salts are selected from calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide, and mixtures thereof.

Preferred amino acids for stabilizing the sweat-inhibiting salts are selected from glycine, alanine, leucine, isoleucine, β-alanine, valine, cysteine, serine, tryptophan, phenylalanine, methionine, β-amino-n-butanoic acid and γ-amino-n-butanoic acid and the salts thereof, in each case in the d form, l form or dl form; glycine is more preferred.

Preferred hydroxyalkanoic acids for stabilizing the sweat-inhibiting salts are selected from glycolic acid and lactic acid.

Further preferred sweat-inhibiting active ingredients are activated aluminum or aluminum zirconium salts, such as are disclosed in U.S. Pat. No. 6,902,723 for example, including 5 to 78 wt. % (USP) of an activated sweat-inhibiting aluminum or aluminum zirconium salt, an amino acid or hydroxyalkanoic acid in an amount to provide a weight ratio of (amino acid or hydroxyalkanoic acid) to (Al+Zr) of 2:1 to 1:20 and preferably 1:1 to 1:10, and a water-soluble strontium salt in an amount to provide a weight ratio of Sr to (Al+Zr) of 1:1 to 1:28 and preferably 1:2 to 1:25.

More preferred solid sweat-inhibiting activated salt compositions, according to U.S. Pat. No. 6,902,723 for example, include 48 to 78 wt. % (USP), preferably 66 to 75 wt. % of an activated aluminum or aluminum zirconium salt and 1 to 16 wt. %, preferably 4 to 13 wt. % of molecularly bound water, also sufficient water-soluble strontium salt that the weight ratio of Sr to (Al+Zr) is 1:1 to 1:28, preferably 1:2 to 1:25, and sufficient amino acid that the weight ratio of amino acid to (Al+Zr) is 2:1 to 1:20, preferably 1:1 to 1:10.

Further more preferred solid sweat-inhibiting activated salt compositions, according to U.S. Pat. No. 6,902,723 for example, include 48 to 78 wt. % (USP), preferably 66 to 75 wt. % of an activated aluminum or aluminum zirconium salt and 1 to 16 wt. %, preferably 4 to 13 wt. % of molecularly bound water, also sufficient water-soluble strontium salt that the weight ratio of Sr to (Al+Zr) is 1:1 to 1:28, preferably 1:2 to 1:25, and sufficient glycine that the weight ratio of glycine to (Al+Zr) is 2:1 to 1:20, preferably 1:1 to 1:10.

Further more preferred solid sweat-inhibiting activated salt compositions, according to U.S. Pat. No. 6,902,723 for example, include 48 to 78 wt. % (USP), preferably 66 to 75 wt. % of an activated aluminum or aluminum zirconium salt and 1 to 16 wt. %, preferably 4 to 13 wt. % of molecularly bound water, also sufficient water-soluble strontium salt that the weight ratio of Sr to (Al+Zr) is 1:1 to 1:28, preferably 1:2 to 1:25, and sufficient hydroxyalkanoic acid that the weight ratio of hydroxyalkanoic acid to (Al+Zr) is 2:1 to 1:20, preferably 1:1 to 1:10.

Further preferred activated aluminum salts are those of the general formula $Al_2(OH)_{6-a}Xa$, in which X is Cl, Br, 1 or $NO_3$ and "a" is a value from 0.3 to 5, preferably from 0.8 to 2.5 and more preferably 1 to 2, such that the molar ratio of Al to X is 0.9:1 to 2.1:1, as is disclosed in U.S. Pat. No. 6,074,632 for example. These salts generally include a little associatively bound water of hydration, typically 1 to 6 mol of water per mol of salt. Aluminum chlorohydrate is more preferred (i.e. X is Cl in the above formula), and specifically 5/6-basic aluminum chlorohydrate, wherein "a" is 1, such that the molar ratio of aluminum to chlorine is 1.9:1 to 2.1:1.

Preferred activated aluminum zirconium salts are those that are mixtures or complexes of the aluminum salts described above with zirconium salts of the formula $ZrO(OH)_{2-pb}Y_b$, in which Y is Cl, Br, 1, $NO_3$ or $SO_4$, b is a rational number from 0.8 to 2 and p is the valence of Y, as disclosed in U.S. Pat. No. 6,074,632 for example. The zirconium salts generally likewise include a little associatively bound water of hydration, typically 1 to 7 mol of water per mol of salt. The zirconium salt is preferably zirconyl hydroxychloride of the formula $ZrO(OH)_{2-b}Cl_b$, in which b is a rational number from 0.8 to 2, preferably 1.0 to 1.9. Preferred aluminum zirconium salts have a molar Al:Zr ratio of 2 to 10 and a metal to (X+Y) ratio of 0.73 to 2.1, preferably 0.9 to 1.5. A more preferred salt is aluminum zirconium chlorohydrate (i.e. X and Y are Cl) with an Al:Zr ratio of 2 to 10 and a molar metal to Cl ratio of 0.9 to 2.1. The term aluminum zirconium chlorohydrate comprises the tri-, tetra-, penta- and octachlorohydrate forms.

Zirconium salts that are preferred according to the invention have the general formula $ZrO(OH)_{2-a}Cl_a \cdot xH_2O$ where a=1.5 to 1.87; x=1 to 7, with a and x being rational numbers. These zirconium salts are disclosed for example in the Belgian publication BE 825146.

Further preferred sweat-inhibiting active ingredients are disclosed in U.S. Pat. No. 6,663,854 and US 20040009133.

The sweat-inhibiting active ingredients can be present both in solubilized and in undissolved, suspended form.

If the sweat-inhibiting active ingredients are present suspended in a water-immiscible carrier, it is preferable for reasons of product stability for the active ingredient particles to have a number-average particle size of 0.1 to 200 μm, preferably 1 to 50 μm, more preferably 3 to 20 μm and exceptionally preferably 5 to 10 μm.

Preferred aluminum salts and aluminum zirconium salts have a molar metal to chloride ratio of 0.9 to 1.3, preferably 0.9 to 1.1, more preferably 0.9 to 1.0.

Preferred aluminum zirconium chlorohydrates generally have the empirical formula $Al_nZr(OH)_{[3n+4-m(n+1)]}(Cl)_{[m(n+1)]}$ where n=2.0 to 10.0, preferably 3.0 to 8.0, m=0.77 to 1.11 (corresponding to a molar metal (Al+Zr) to chloride ratio of 1.3 to 0.9), preferably m=0.91 to 1.11 (corresponding to M:Cl=1.1 to 0.9), and more preferably m=1.00 to 1.11 (corresponding to M:Cl=1.0 to 0.9), furthermore very preferably m=1.02 to 1.11 (corresponding to M:Cl=0.98 to 0.9) and very preferably m=1.04 to 1.11 (corresponding to M:Cl=0.96 to 0.9).

These salts generally include a little associatively bound water of hydration, typically 1 to 6 mol of water per mol of salt, corresponding to 1 to 16 wt. %, preferably 4 to 13 wt. % of water of hydration.

The preferred aluminum zirconium chlorohydrates are conventionally associated with an amino acid to prevent polymerization of the zirconium species during production. Preferred stabilizing amino acids are selected from glycine, alanine, leucine, isoleucine, β-alanine, cysteine, valine, serine, tryptophan, phenylalanine, methionine, β-mino-n-butanoic acid and γ-amino-n-butanoic acid and the salts thereof, in each case in the d form, l form or dl form; glycine is more preferred. The amino acid is included in the salt in an amount from 1 to 3 mol, preferably 1.3 to 1.8 mol, in each case per mol of zirconium.

Preferred sweat-inhibiting salts are aluminum zirconium tetrachlorohydrate (Al:Zr=2-6; M:Cl=0.9-1.3), in particular salts with a molar metal to chloride ratio of 0.9 to 1.1, preferably 0.9 to 1.0.

Also preferred according to the invention are aluminum zirconium chlorohydrate glycine salts stabilized with betaine (($CH_3$)$_3$N$^+$—$CH_2$—COO$^-$). More preferred corresponding compounds have a molar total (betaine+glycine)/Zr ratio of (0.1 to 3.0):1, preferably (0.7 to 1.5):1, and a molar ratio of betaine to glycine of at least 0.001:1. Corresponding compounds are disclosed in U.S. Pat. No. 7,105,691 for example.

In a more preferred embodiment according to the invention an "activated" salt is included as a particularly effective antiperspirant salt, in particular one with a high HPLC peak 5 aluminum content, in particular with a peak 5 surface area of at least 33%, more preferably at least 45%, relative to the total surface area under peaks 2 to 5, measured by HPLC of a 10 wt. % aqueous solution of the active ingredient under conditions in which the aluminum species is dissolved into at least 4 successive peaks (referred to as peaks 2 to 5). Preferred aluminum zirconium salts having a high HPLC peak 5 aluminum content (also referred to as "E$^5$AZCH") are disclosed in U.S. Pat. No. 6,436,381 and U.S. Pat. No. 6,649,152 for example.

Such activated "E$^5$AZCH" salts are also preferred in which the HPLC peak 4 to peak 3 surface area ratio is at least 0.4, preferably at least 0.7, more preferably at least 0.9.

Further more preferred antiperspirant active ingredients are aluminum zirconium salts having a high HPLC peak 5 aluminum content that are additionally stabilized with a water-soluble strontium salt and/or with a water-soluble calcium salt. Corresponding salts are disclosed in U.S. Pat. No. 6,923,952 for example.

Further preferred antiperspirant active ingredients are selected from astringent titanium salts such as are disclosed in GB 2299506 A for example.

The antiperspirant active ingredients can be used as non-aqueous solutions or as glycolic solubilizates.

In a more preferred embodiment the composition includes an astringent aluminum salt, in particular aluminum chlorohydrate, which is sold for example in powder form as Micro Dry® Ultrafine or Superultrafine by Reheis, Microdry 323 by Summit, as Chlorhydrol® and in activated form as Reach® 501 by Reheis. An aluminum sesquichlorohydrate that is likewise more preferred is offered by Reheis under the name Reach® 301. Activated aluminum chlorohydrates that are available under the names Reach® 101 and Reach® 103, AACH-7171 from Reheis or Summit are also more preferred. The use of aluminum zirconium tetrachlorohydrex glycine complexes, which are commercially available in powder form under the name Rezal® 36 GP from Reheis or AZG-364 or 369 from Summit, in activated grade, as Reach® 908, can also be more preferred according to the invention. Aluminum zirconium pentachlorohydrex glycine complexes (AAZG-3108 or AAZG-3110 from Summit) can also be used.

The composition according to the invention must also include at least one oil in said total amount. An oil is understood according to the invention to be a liquid substance that is less than 1 wt. % miscible in bidistilled water under normal conditions.

It is preferable according to the invention for oils to be included in the composition according to the invention in a total amount, relative to the weight of the composition, of 30 to 80 wt. %, more preferably 40 to 75 wt. %, particularly preferably 45 to 70 wt. %.

The composition according to the invention more preferably includes at least one volatile oil as the oil. It is in turn preferable for the volatile oils to be included in the composition according to the invention in a total amount, relative to the weight of the composition, of 30 to 80 wt. %, more preferably 40 to 75 wt. %, particularly preferably 45 to 70 wt. %.

A volatile oil is understood according to the invention to refer to oils that have a vapor pressure of 0.01 kPa or more at 293.15 K.

Oils that are preferred according to the invention are selected from silicone oils, which include for example dialkyl and alkylaryl siloxanes, such as for example cyclopentasiloxane, cyclohexasiloxane, dimethyl polysiloxane and methylphenyl polysiloxane, but also hexamethyl disiloxane, octamethyl trisiloxane and decamethyl tetrasiloxane.

More preferred volatile oils are volatile silicone oils and volatile non-silicone oils. Volatile silicone oils, which can be cyclic, such as for example octamethyl cyclotetrasiloxane, decamethyl cyclopentasiloxane and mixtures thereof, such as are included for example in the commercial products DC 244, 245, 344 and 345 from Dow Corning, are preferred according to the invention. Volatile linear silicone oils are likewise more preferred, in particular hexamethyl disiloxane ($L_2$), octamethyl trisiloxane ($L_3$), decamethyl tetrasiloxane ($L_4$) and any two-component and three-component mixtures of $L_2$, $L_3$ and/or $L_4$, preferably mixtures such as are included for example in the commercial products DC2-1184, Dow Corning® 200 (0.65 cSt) and Dow Corning® 200 (1.5 cSt) from Dow Corning.

Volatile silicone oils are outstandingly suitable according to the invention because they impart a pleasant skin feel to the composition according to the invention, with little staining of clothing. Compositions that are more preferred according to the invention are thus characterized in that they include at least one volatile silicone oil. It is in turn preferable for the volatile silicone oils to be included in the composition according to the invention in a total amount, relative to the weight of the composition, of 20 to 80 wt. %, in particular 30 to 80 wt. %, more preferably 40 to 75 wt. %, particularly preferably 45 to 70 wt. %.

In addition to or in place of the at least one volatile silicone oil, at least one volatile non-silicone oil can also be included. Preferred volatile non-silicone oils are selected from $C_8$-$C_{16}$ isoparaffins, in particular from isodecane, isododecane, isotetradecane and isohexadecane, as well as mixtures thereof. C10-13 isoparaffin (e.g. the commercial product Pioneer 2094 from Hanson & Rosenthal) is preferably suitable in particular.

This at least one volatile non-silicone oil is also preferably included in a total amount of 20 to 80 wt. %, more preferably 30 to 80 wt. %, particularly preferably 40 to 75 wt. %, relative in each case to the total weight of the composition.

Owing to the skin feel and the stability of the resulting compositions, silicone oils are preferred over isoparaffins as the volatile oil.

In addition to the aforementioned substances conventionally referred to as volatile silicone oils and in addition to the aforementioned volatile non-silicone oils, the compositions according to the invention can additionally include at least one non-volatile oil selected from non-volatile silicone oils and non-volatile non-silicone oils.

Preferred non-volatile silicone oils are selected from higher-molecular-weight linear dimethyl polysiloxanes, available commercially for example under the name Dow Corning® 190, Dow Corning® 200 Fluid with kinematic viscosities (25° C.) in the range from 5 to 100 cSt, preferably 5 to 50 cSt or 5 to 10 cSt, and Baysilon® 350 M with a kinematic viscosity (25° C.) of approximately 350 cSt.

Non-volatile silicone oils that are likewise preferred according to the invention are selected from silicones of formula (Sil-1), in which x is selected from whole numbers from 1 to 20, preferably 1 to 3.

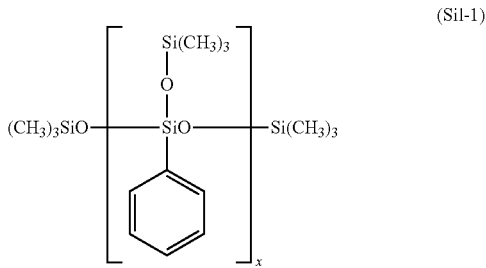

A preferred silicone oil of formula (Sil-1) is available under the INCI name Phenyl Trimethicone.

Natural and synthetic hydrocarbons, such as for example paraffin oils, $C_{18}$-$C_{30}$ isoparaffins, in particular isoeicosane, polyisobutenes or polydecenes, which are available for example under the name Emery® 3004, 3006, 3010 or under the name Ethylflo® from Albemarle or Nexbase® 2004G from Nestle, as well as 1,3-di-(2-ethylhexyl)cyclohexane (available for example under the trade name Cetiol® S from Cognis), likewise belong to the non-volatile non-silicone oils that are preferred according to the invention.

Further non-volatile non-silicone oils that are preferred according to the invention are selected from the benzoic acid esters of linear or branched $C_{8-22}$ alkanols. Benzoic acid C12-C15 alkyl esters, available for example as the commercial product Finsolv® TN, benzoic acid isostearyl esters, available for example as the commercial product Finsolv® SB, ethylhexyl benzoate, available for example as the commercial product Finsolv® EB, and benzoic acid octyl dodecyl esters, available for example as the commercial product Finsolv® BOD, are more preferred.

Further non-volatile non-silicone oils that are preferred according to the invention are selected from the triglycerides of linear or branched, saturated or unsaturated, optionally hydroxylated $C_{8-30}$ fatty acids. The use of natural oils, for example soybean oil, cottonseed oil, sunflower oil, palm oil, palm kernel oil, linseed oil, almond oil, castor oil, corn oil, rapeseed oil, olive oil, sesame oil, thistle oil, wheat germ oil, peach kernel oil and the liquid components of coconut butter and the like, can be particularly suitable. Synthetic triglyceride oils are also suitable, however, in particular capric/caprylic triglycerides, for example the commercial products Myritol® 318, Myritol® 331 (Cognis) or Miglyol® 812 (Hüls) with unbranched fatty acid esters, as well as glyceryl triisostearin and the commercial products Estol® GTEH 3609 (Uniqema) or Myritol® GTEH (Cognis) with branched fatty acid esters.

Further non-volatile non-silicone oils that are more preferred according to the invention are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Further non-volatile non-silicone oils that are more preferred according to the invention are selected from the esters of linear or branched saturated or non-volatile non-silicone oils, esters of unsaturated alkanols having 2 to 30 carbon atoms with linear or branched saturated or unsaturated fatty acids having 2 to 30 carbon atoms, which can be hydroxylated. These include hexyldecyl stearate (Eutanol® G 16 S), hexyldecyl laurate, isodecyl neopentanoate, isononyl isononanoate, 2-ethylhexyl palmitate (Cegesoft® C 24) and 2-ethylhexyl stearate (Cetiol® 868). Likewise preferred are isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-thylhexyl cocoate, 2-octyldodecyl palmitate, butyl octanoic acid-2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate and dipalmitate.

Further non-volatile non-silicone oils that are more preferred according to the invention are selected from the addition products of 1 to 5 propylene oxide units with mono- or polyhydric $C_{8-22}$ alkanols such as octanol, decanol, decanediol, lauryl alcohol, myristyl alcohol and stearyl alcohol, for example PPG-2 myristyl ether and PPG-3 myristyl ether (Witconol® APM).

Further non-volatile non-silicone oils that are more preferred according to the invention are selected from the addition products of at least 6 ethylene oxide and/or propylene oxide units with mono- or polyhydric $C_{3-22}$ alkanols such as glycerol, butanol, butanediol, myristyl alcohol and stearyl alcohol, which can be esterified if desired, for example PPG-14 butyl ether (Ucon Fluid® AP), PPG-9 butyl ether (Breox® B25), PPG-10 butanediol (Macol® 57), PPG-15 stearyl ether (Arlamol® E) and Glycereth-7 diisononanoate.

Further non-volatile non-silicone oils that are more preferred according to the invention are selected from the $C_8$-$C_{22}$ alkanol esters of monobasic or polybasic $C_2$-$C_7$ hydroxycarboxylic acids, in particular the esters of glycolic acid, lactic acid, malic acid, tartaric acid, citric acid and salicylic acid. Such esters based on linear $C_{14/15}$ alkanols, for example $C_{12}$-$C_{15}$ alkyl lactate, and on $C_{12/13}$ alkanols branched in 2-position are available under the trademark Cosmacol® from Nordmann, Rassmann GmbH & Co, Hamburg, in particular the commercial products Cosmacol® ESI, Cosmacol® EMI and Cosmacol® ETI.

Further non-volatile non-silicone oils that are more preferred according to the invention are selected from the symmetrical, asymmetrical or cyclic esters of carbonic acid with alkanols, for example glycerol carbonate, dicaprylyl carbonate (Cetiol® CC) or the esters according to the teaching of DE 19756454 A1.

Further oils that can be preferred according to the invention are selected from the esters of dimers of unsaturated $C_{12}$-$C_{22}$ fatty acids (dimer fatty acids) with monohydric linear, branched or cyclic $C_2$-$C_{18}$ alkanols or with polyhydric linear or branched $C_2$-$C_6$ alkanols.

It is preferable according to the invention for the compositions according to the invention to include the non-volatile oils in a total amount of 0 to 20 wt. %, in particular 0 to 10 wt. %, relative to the total weight of the composition.

The composition according to the invention must include a defined mixture of fatty alcohols.

It is preferable according to the invention for the fatty alcohols used to produce the composition according to the invention to be in solid form and for all definitions relating to fatty alcohols to relate to solid fatty alcohols within the meaning of the application and for liquid fatty alcohols to be attributed exclusively to the oil component of the composition according to the invention.

In a composition that is preferred according to the invention the total amount of fatty alcohols relative to the total weight of the composition is 4 to 9 wt. %.

It is preferable according to the invention for the composition to include the fatty alcohols having 18 carbon atoms in a total amount of 2.0 to 5.0 wt. %, relative to the total weight of the composition.

It is preferable according to the invention for the composition to include the fatty alcohols having 20 to 28 carbon atoms in a total amount of 0.8 to 2.0 wt. %, relative to the total weight of the composition.

It is preferable according to the invention for the composition to include the fatty alcohols having 30 to 38 carbon atoms in a total amount of 0.6 to 1.5 wt. %, relative to the total weight of the composition.

It is preferable according to the invention for the composition to include the fatty alcohols having 40 to 48 carbon atoms in a total amount of 0.2 to 0.7 wt. %, relative to the total weight of the composition.

Initially independently thereof, it is preferable for the composition according to the invention to include less than 0.05 wt. % of fatty alcohols having more than 50 carbon atoms, relative to the total weight of the composition.

Initially independently thereof, it is preferable for the weight ratio of (in particular solid) fatty alcohols having 12 to 18 carbon atoms to the other fatty alcohols to be in a weight ratio range from 1:1 to 1:1.3.

Initially independently thereof, it is preferable for the weight ratio of (in particular solid) fatty alcohols having 20 to 28 carbon atoms to fatty alcohols having 30 to 38 carbon atoms to be in a weight ratio range from 1:0.5 to 1:2, in particular from 1:0.9 to 1:0.6.

Initially independently thereof, it is preferable for the weight ratio of (in particular solid) fatty alcohols having 20 to 28 carbon atoms to fatty alcohols having 40 to 48 carbon atoms to be in a weight ratio range from 1:0.1 to 1:1, in particular from 1:0.2 to 1:0.4.

It is in turn more preferable according to the invention if
(i) the weight ratio of (in particular solid) fatty alcohols having 12 to 18 carbon atoms to the other fatty alcohols is in a weight ratio range from 1:1 to 1:3, in particular from 1:1 to 1:1.3,
and
(ii) the weight ratio of (in particular solid) fatty alcohols having 20 to 28 carbon atoms to fatty alcohols having more than 28 carbon atoms is distributed as follows:
(ii-1) the weight ratio of (in particular solid) fatty alcohols having 20 to 28 carbon atoms to fatty alcohols having 30 to 38 carbon atoms is in a weight ratio range from 1:0.5 to 1:2, in particular from 1:0.9 to 1:0.6,
and/or
(ii-2) the weight ratio of (in particular solid) fatty alcohols having 20 to 28 carbon atoms to fatty alcohols having 40 to 48 carbon atoms is in a weight ratio range from 1:0.1 to 1:1, in particular from 1:0.2 to 1:0.4.

Further preferred compositions according to the invention are characterized in that they additionally include at least one solid, water-insoluble particulate filler, to improve the consistency and the sensory properties for example. In an exceptionally preferred embodiment this filler is selected from optionally modified starches (obtained for example from corn, rice, potatoes) and starch derivatives, which are optionally pre-gelatinized (for example DRY FLO PC from AKZO), silicon dioxide, silicas, for example Aerosil® types, spherical polyalkyl sesquisiloxane particles (in particular Aerosil® R972 and Aerosil® 200V from Degussa), silica gels, talc, kaolin, magnesium aluminum silicates, boron nitride, lactoglobulin derivatives, for example sodium $C_{8-16}$ isoalkyl succinyl lactoglobulin sulfonate, obtainable from Brooks Industries as the commercial product Biopol® OE, glass powders, polymer powders, consisting in particular of polyolefins, polycarbonates, polyurethanes, polyamides, for example nylon, polyesters, polystyrenes, polyacrylates, (meth)acrylate or (meth)acrylate-vinylidene copolymers, which can be crosslinked, or silicones, as well as mixtures of these substances.

Polymer powders based on a polymethacrylate copolymer are available for example as the commercial product Polytrap® 6603 (Dow Corning). Other polymer powders, based for example on polyamides, are available under the name Orgasol® 1002 (polyamide 6) and Orgasol® 2002 (polyamide 12) from Elf Atochem. Further polymer powders that are suitable as preferred fillers according to the invention are for example polymethacrylates (Micropearl® M from SEPPIC or Plastic Powder A from NIKKOL), styrene-divinyl benzene copolymers (Plastic Powder FP from NIKKOL), polyethylene and polypropylene powders (ACCUREL® EP 400 from AKZO) or silicone polymers (Silicone Powder X2-1605 from Dow Corning).

Preferred compositions according to the invention are characterized in that they include at least one solid, water-insoluble particulate filler in a total amount of 1 to 99 wt. %, preferably 2 to 90 wt. %, more preferably 3 to 15 wt. %, exceptionally preferably 4, 5, 6, 7, 8, 9, 10, 11, 12, 13 and 14 wt. %, relative in each case to the total composition.

Further preferred compositions according to the invention are therefore characterized in that they additionally include at least one lipophilic thickening agent.

Lipophilic thickening agents that are preferred according to the invention are selected from hydrophobed clay minerals, fumed silicas, ethylene/propylene/styrene copolymers, butylene/ethylene/styrene copolymers, dextrin esters, silicone elastomers, waxes that are solid under normal conditions and/or glycerol triesters. The composition according to the invention more preferably additionally includes at least one silicone elastomer as the lipophilic thickening agent.

Preferred hydrophobed clay minerals are selected from hydrophobed montmorillonites, hydrophobed hectorites and hydrophobed bentonites, more preferably from disteardimonium hectorite, stearalkonium hectorite, quaternium-18 hectorite and quaternium-18 bentonite. The commercial thickening agents provide these hydrophobed clay minerals in the form of a gel in an oil component, preferably in cyclomethicone, and/or in a non-silicone oil component, such as propylene carbonate for example. Such gels are obtainable for example under the commercial name Bentone® or Thixogel.

Compositions that are preferred according to the invention are characterized in that they include at least one hydrophobed clay mineral in a total amount of 0.5 to 10 wt. %, preferably 1 to 7 wt. %, more preferably 2 to 6 wt. %, exceptionally preferably 3 to 5 wt. %, relative in each case to the total weight of the composition according to the invention.

Further lipophilic thickening agents that are preferred according to the invention are selected from fumed silicas, for example the commercial products of the Aerosil® range from Evonik Degussa. Hydrophobed fumed silicas are more preferred, more preferably silica silylate and silica dimethyl silylate.

Compositions that are preferred according to the invention are characterized in that they include at least one fumed silica, preferably at least one (preferably hydrophobed) fumed silica, in a total amount of 0.5 to 10 wt. %, preferably 1 to 7 wt. %, more preferably 2 to 6 wt. %, exceptionally preferably 3 to 5 wt. %, relative in each case to the total weight of the composition according to the invention.

Further compositions that are preferred according to the invention are characterized in that they include at least one hydrophobed fumed silica and at least one hydrophilic silica.

Further lipophilic thickening agents that are preferred according to the invention are selected from ethylene/propylene/styrene copolymers and butylene/ethylene/styrene copolymers. The copolymers are more preferably used as a pre-thickened oil-based gel. Such gels are obtainable for example under the commercial name Versagel® (from Penreco). Gels with mineral oil, hydrogenated polyisobutene, isoparaffins, such as isohexadecane or isododecane, and with ester oils, in particular with isopropyl palmitate or isopropyl myristate, are preferred.

Compositions that are preferred according to the invention are characterized in that they include at least one ethylene/propylene/styrene copolymer and/or butylene/ethylene/styrene copolymer in a total amount of 0.05 to 3 wt. %, preferably 0.1 to 2 wt. %, more preferably 0.2 to 1.0 wt. %, exceptionally preferably 0.3 to 0.5 wt. %, relative in each case to the total weight of the composition according to the invention.

Further lipophilic thickening agents that are preferred according to the invention are selected from silicone elastomers. A further preferred embodiment of the invention is characterized in that at least one silicone elastomer, which is obtainable by crosslinking an organopolysiloxane having at least two $C_2$-$C_{10}$ alkenyl groups with a terminal double bond in each molecule with an organopolysiloxane having at least two silicone-bound hydrogen atoms in each molecule, is included.

Organopolysiloxanes having at least two $C_2$-$C_{10}$ alkenyl groups with a terminal double bond in the molecule that are more preferred according to the invention are selected from methylvinylsiloxanes, methylvinylsiloxane-dimethylsiloxane copolymers, dimethylpolysiloxanes with dimethylvinylsiloxy end groups, dimethylsiloxane-methylphenylsiloxane copolymers with dimethylvinylsiloxy end groups, dimethylsiloxane-diphenylsiloxane-methylvinylsiloxane copolymers with dimethylvinylsiloxy end groups, dimethylsiloxane-methylvinylsiloxane copolymers with trimethylsiloxy end groups, dimethylsiloxane-methylphenylsiloxane-methylvinylsiloxane copolymers with trimethylsiloxy end groups, methyl-(3,3,3-trifluoropropyl)polysiloxanes with dimethylvinylsiloxy end groups and dimethylsiloxane-methyl-(3,3,3-trifluoropropyl)siloxane copolymers with dimethylvinylsiloxy end groups.

Crosslinking organopolysiloxanes having at least two silicone-bound hydrogen atoms that are more preferred according to the invention are selected from methyl hydrogen polysiloxanes with trimethylsiloxy end groups, dimethylsiloxane-methyl hydrogen siloxane copolymers with trimethylsiloxy end groups and cyclic dimethylsiloxane-methyl hydrogen siloxane copolymers.

More preferred silicone elastomers according to the invention which as a raw material are already present pre-swollen in a silicone that is liquid at room temperature under normal conditions and which constitute a silicone-based gel are commercially available, for example under the trade names Dow Corning 9040 Silicone Elastomer Blend (a cyclomethicone (and) dimethicone crosspolymer from Dow Corning; silicone elastomer content 12-13 wt. %), SFE 168, a cyclomethicone (and) dimethicone/vinyl dimethicone crosspolymer from GE Silicones, vinyl dimethicone crosspolymers, included in KSG-15 (cyclomethicone (and) dimethicone/vinyl dimethicone crosspolymer, silicone elastomer content 4-10 wt. %), KSG-16 (dimethicone (and) dimethicone/vinyl dimethicone crosspolymer, silicone elastomer content 20-30 wt. %), KSG-17 (cyclomethicone (and) dimethicone/vinyl dimethicone crosspolymer), KSG-18 (phenyl trimethicone (and) dimethicone/phenyl vinyl dimethicone crosspolymer, silicone elastomer content 10-20 wt. %); and KSG-20, obtainable from Shin Etsu Silicones of America (Akron, Ohio), and from Grant Industries Inc. (Elmwood Park, N.J.) the products from the Gransil® range, in particular Gransil SR-CYC (cyclomethicone and stearylvinyl/hydromethylsiloxane copolymer), Gransil® RPS Gel (INCI name: Cyclopentasiloxane and Polysilicone-11), Gransil® GCM-4 (INCI name: Cyclotetrasiloxane and Polysilicone-11), Gransil® GCM-5 (INCI name: Cyclopentasiloxane and Polysilicone-11), Gransil® RPS (INCI name: Cyclopentasiloxane and Polysilicone-11), GI-CD 10 (INCI name: Cyclopentasiloxane (and) Stearoxymethicone/Dimethicone Copolymer (and) Dimethicone), Gransil® IDS (INCI name: Isododecane (and) Cyclotetrasiloxane (and) Polysilicone-11), Gransil® PC-12 (INCI name: Isododecane (and) Polysilicone-11), Gransil® IDS-5 (INCI name: Isododecane (and) Cyclopentasiloxane (and) Polysilicone-11), Gransil® APK-1 (INCI name: Dimethicone and Cyclopentasiloxane and Polysilicone-11 and Nylon-12 and Methyl Methacrylate/Acrylonitrile Copolymer and PEG-10 Dimethicone and Polysorbate-40 and Isohexadecane and Ammonium Polyacryloyldimethyl Taurate), Gransil® DMCM-5 (INCI name: Dimethicone and Cyclopentasiloxane and Polysilicone-11), Gransil® DMG-6 with dimethicone (6 cSt) (INCI name: Dimethicone and Polysilicone-11), Gransil® DMG-20 with dimethicone (20 cSt) (INCI name: Dimethicone and Polysilicone-11), Gransil® AM-8 Gel (INCI name: Caprylyl Methicone and Cyclopentasiloxane and Polysilicone-11), Gransil® DM 5 with dimethicone (5 cSt) (INCI name: Dimethicone and Polysilicone-11), Gransil® DMID (INCI name: Dimethicone and Isododecane and Polysilicone-11), Gransil® PM (INCI name: Phenyl Trimethicone and Polysilicone-11), Gransil® ININ (INCI name: Isononyl Isononanoate (and) Polysilicone-11).

Silicone elastomers which as a raw material are already present pre-swollen in a silicone that is liquid at room temperature under normal conditions, mixed with a non-silicone-including oil, fat or wax, and which constitute a silicone-/non-silicone-based gel can likewise be used to advantage in the compositions according to the invention. Such silicone elastomer compositions are likewise commercially available, for example under the trade names Gransil® MLB (INCI name: Cyclopentasiloxane and Polysilicone-11 and Beeswax), Gransil® PS (INCI name: Cyclotetrasiloxane and Polysilicone-11 and Petrolatum), Gransil® PS-5 (INCI name: Cyclopentasiloxane and Polysilicone-11 and Petrolatum), Gransil® DMG-20 P with dimethicone (20 cSt) and petrolatum (INCI name: Dimethicone and Polysilicone-11 and Petrolatum), Gransil®RJO (INCI name: Cyclopentasiloxane and Polysilicone-11 and Jojoba Oil), Gransil® LANO (INCI name: Cyclopentasiloxane and Polysilicone-11 and Lanolin), Gransil® OHS-5 (INCI name: Cyclopentasiloxane and Polysilicone-11 and Octyl Hydroxystearate) and Gransil® DML (INCI name: Dimethicone (and) Neopentyl Glycol Diheptanoate (and) Polysilicone-11).

A further preferred embodiment of the invention is characterized in that the silicone elastomer is obtainable by crosslinking an organopolysiloxane including at least two $C_2$-$C_{10}$ alkenyl groups with a terminal double bond in each molecule with at least one alpha,omega-diene. Crosslinked alpha,omega-dienes that are more preferred according to the invention have the formula $CH_2=CH(CH_2)_xCH=CH_2$ where x=1-20. More preferred alpha,omega-dienes are selected from 1,4-pentadiene, 1,5-hexadiene, 1,6-heptadiene, 1,7-ctadiene, 1,8-nonadiene, 1,11-dodecadiene, 1,13-tetradecadiene and 1,19-eicosadiene.

Compositions that are preferred according to the invention are characterized in that they include at least one silicone elastomer in a total amount of 0.05 to 3 wt. %, preferably 0.1 to 2 wt. %, more preferably 0.2 to 1.0 wt. %, exceptionally preferably 0.3 to 0.5 wt. %, relative in each case to the total weight of the composition according to the invention.

The agent according to the invention preferably additionally includes at least one polyethylene wax as the wax that is solid under normal conditions. Preferably suitable polyethylene waxes have 30 to 60 carbon atoms.

Further preferred compositions according to the invention are characterized in that they include at least one scent and/or at least one perfume oil.

Individual fragrance compounds, for example the synthetic products of the ester, ether, aldehyde, ketone, alcohol and hydrocarbon type, can be used as scents or perfume oils. The phenolic fragrance compounds include for example carvacrol. Fragrance compounds of the ester type are for example benzyl acetate, methyl anthranilate, ortho-t-butyl cyclohexyl acetate, p-tert-butyl cyclohexyl acetate, diethyl phthalate, nonanediol-1,3-diacetate, isononyl acetate, isononyl formate, phenylethyl phenyl acetate, phenoxyethyl isobutyrate, linalyl acetate, dimethyl benzylcarbinyl acetate, phenylethyl acetate, linalyl benzoate, benzyl formate, ethyl methylphenyl glycinate, allyl cyclohexyl propionate, styrallyl propionate, benzyl salicylate, ethyl salicylate, isoamyl salicylate, hexyl salicylate and 4-nonanolide. The ethers include for example benzyl ethyl ethers, the aldehydes include for example the linear alkanals having 8 to 18 C atoms, citral, citronellal, citronellyl oxyacetaldehyde, cyclamen aldehyde, hydroxycitronellal, lilial and bourgeonal, the ketones include for example 6-acetyl-1,1,3,4,4,6-hexamethyl tetrahydronaphthalene, para-t-amylcyclohexanone, 2-n-heptylcyclopentanone, n-methyl naphthyl ketone and the ionones α-isomethyl ionone and methyl cedryl ketone, the alcohols include cinnamic alcohol, anethol, citronellol, dimyrcetol, eugenol, geraniol, linalool, phenylethyl alcohol and terpineol, the hydrocarbons include 1,3,4,6,7,8-hexahydro-4,6,6,7,8,8-hexamethyl cyclopenta-a-2-benzopyrane, hydroxymethyl isopropyl cyclopentane, 3-a-methyl dodecahydro-6,6,9a-trimethylnaphtho-2(2,1-b)furane, isobutyl quinoline as well as the terpenes and balsams. Mixtures of different fragrances which together generate an attractive scent note are preferably used.

Suitable perfume oils can also include natural fragrance mixtures, such as are obtainable from plant or animal sources, for example pine, citrus, jasmine, rose, lily or ylang-ylang oil. Low-volatility essential oils, which are mostly used as aroma components, are also suitable as perfume oils, for example sage oil, chamomile oil, melissa oil, mint oil, cinnamon leaf oil, lime blossom oil, juniper berry oil, vetiver oil, oliban oil, galbanum oil, laudanum oil, clove oil, iso-eugenol, thyme oil, bergamot oil, geranium oil and rose oil.

Compositions that are preferred according to the invention include at least one scent and/or at least one perfume oil in a total amount of 0.01 to 10 wt. %, preferably 0.1 to 5 wt. %, more preferably 0.5 to 3 wt. %, exceptionally preferably 1 to 2 wt. %, relative in each case to the total weight of the composition according to the invention.

Preferred compositions according to the invention are characterized in that they additionally include at least one deodorant active ingredient. Preferred such deodorant active ingredients are selected from odor absorbers, deodorizing ion-exchangers, bacteriostatic substances, substances having a prebiotic effect and enzyme inhibitors and, more preferably, combinations of said deodorant active ingredients.

Silicates serve as odor absorbers, which at the same time advantageously also support the rheological properties of the composition according to the invention. The silicates that are particularly advantageous according to the invention include above all phyllosilicates and of those in particular montmorillonite, kaolinite, illite, beidellite, nontronite, saponite, hectorite, bentonite, smectite and talc. Further advantageous odor absorbers are for example zeolites, zinc ricinoleate, cyclodextrins, certain metal oxides, such as for example aluminum oxide, and chlorophyll.

Bacteriostatic or antimicrobial active ingredients are understood according to the invention to be active ingredients that reduce the number of skin bacteria involved in odor formation or inhibit their growth. These bacteria include inter alia various species from the group of Staphylococci, the group of *Corynebacteria, Anaerococci and Micrococci.*

Organohalogen compounds and organohalides, quaternary ammonium compounds, a series of plant extracts and zinc compounds are preferred in particular according to the invention as bacteriostatic or antimicrobial active ingredients. These include inter alia triclosan, chlorhexidine and chlorhexidine gluconate, 3,4,4'-richlorocarbanilide, bromochlorophene, dichlorophene, chlorothymol, chloroxylenol, hexachlorophene, dichloro-m-xylenol, dequalinium chloride, domiphen bromide, ammonium phenol sulfonate, benzalkonium halides, benzalkonium cetyl phosphate, benzalkonium saccharinates, benzethonium chloride, cetyl pyridinium chloride, lauryl pyridinium chloride, lauryl isoquinolinium bromide, methylbenzethonium chloride. Phenol, disodium dihydroxyethyl sulfosuccinyl undecylenate, sodium bicarbonate, zinc lactate, sodium phenol sulfonate and zinc phenol sulfonate, ketoglutaric acid, terpene alcohols such as for example farnesol, chlorophyllin copper complexes, α-onoalkyl glycerol ethers having a branched or linear saturated or unsaturated, optionally hydroxylated $C_6$-$C_{22}$ alkyl residue, more preferably α-(2-ethylhexyl)glycerol ether, available commercially as Sensiva® SC 50 (from Schillke & Mayr), carboxylic acid esters of mono-, di- and triglycerol (for example glycerol monolaurate, diglycerol monocaprinate), lantibiotics and plant extracts (for example green tea and constituents of linden blossom oil) can also be used.

Further preferred deodorant active ingredients are selected from components having a prebiotic effect, which are understood according to the invention to be components that inhibit only or at least predominantly the odor-forming bacteria of the skin microflora but not the desirable, i.e. non-odor-forming bacteria that belong to a healthy skin microflora. These explicitly include the active ingredients disclosed in the laidopen patent applications DE 10333245 and DE 10 2004 011 968 as having a prebiotic effect; among them are conifer extracts, in particular from the group of Pinaceae, and plant extracts from the group of Sapindaceae, Araliaceae, Lamiaceae and Saxifragaceae, in particular extracts of *Picea* spp., *Paullinia* sp., *Panax* sp., Lamium album or *Ribes nigrum*, and mixtures of these substances.

Enzyme inhibitors include substances that inhibit the enzymes responsible for breaking down sweat, in particular arylsulfatase, β-glucuronidase, aminoacylase, esterases, lipases and/or lipoxigenase, for example trialkyl citric acid esters, in particular triethyl citrate, or zinc glycinate.

Preferred compositions according to the invention are characterized in that the at least one additional deodorant active ingredient is selected from arylsulfatase inhibitors, β-glucuronidase inhibitors, aminoacylase inhibitors, esterase inhibitors, lipase inhibitors and lipoxigenase inhibitors, α-monoalkyl glycerol ethers having a branched or linear saturated or unsaturated, optionally hydroxylated $C_6$-$C_{22}$ alkyl residue, in particular α-(2-ethylhexyl)glycerol ether, components having a prebiotic effect, trialkyl citric acid esters, in particular triethyl citrate, active ingredients that reduce the number of skin bacteria from the group of Staphylococci, Corynebacteria, Anaerococci and Micrococci, which are involved in odor formation, or inhibit their growth, zinc compounds, in particular zinc phenol sulfonate and zinc ricinoleate, organohalogen compounds, in particular triclosan, chlorhexidine, chlorhexidine gluconate and benzalkonium halides, quaternary ammonium compounds, in particular cetyl pyridinium chloride, odor absorbers, in particular silicates and zeolites, sodium bicarbonate, lantibiotics, and mixtures of the aforementioned substances.

Further preferred compositions according to the invention are characterized in that the at least one additional deodorant active ingredient is included in a total amount of 0.1 to 10 wt. %, preferably 0.2 to 7 wt. %, more preferably 0.3 to 5 wt. %, relative to the total weight of active substance in the total composition.

Antioxidative substances can counteract the oxidative decomposition of sweat components and thus inhibit the development of odors. Suitable antioxidants are imidazole and imidazole derivatives (e.g. urocanic acid), peptides such as for example D,L-carnosine, D-carnosine, L-carnosine and derivatives thereof (e.g. anserine), carotinoids, carotene (e.g. α-carotene, β-carotene, lycopene) and derivatives thereof, lipoic acid and derivatives thereof (e.g. dihydrolipoic acid), aurothioglucose, propylthiouracil and other thio compounds (e.g. thioglycerol, thiosorbitol, thioglycolic acid, thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) as well as sulfoximine compounds (e.g. buthionine sulfoximine, homocysteine sulfoximine, buthionine sulfone, penta-, hexa-, heptathionine sulfoximine) in very small acceptable doses (e.g. pmol/kg to μmol/kg), also metal chelators (e.g. α-hydroxy fatty acids, EDTA, EGTA, lactoferrin), humic acids, bile acid, bile extracts, catechins, bilirubin, biliverdin and derivatives thereof, unsaturated fatty acids and derivatives thereof (e.g. γ-linolenic acid, linoleic acid, arachidonic acid, oleic acid), folic acid and derivatives thereof, hydroquinone and derivatives thereof (e.g. arbutin), ubiquinone and ubiquinol and derivatives thereof, vitamin C and derivatives thereof (e.g. ascorbyl palmitate, stearate, dipalmitate, acetate, Mg ascorbyl phosphates, sodium and magnesium ascorbate, disodium ascorbyl phosphate and sulfate, potassium ascorbyl tocopheryl phosphate, chitosan ascorbate), isoascorbic acid and derivatives thereof, tocopherols and derivatives thereof (e.g. tocopheryl acetate, linoleate, oleate and succinate, to cophereth-5, tocophereth-10, tocophereth-12, tocophereth-18, tocophereth-50, tocophersolan), vitamin A and derivatives (e.g. vitamin A palmitate), the coniferyl benzoate of benzoic resin, rutin, rutic acid and derivatives thereof, disodium rutinyl disulfate, cinnamic acid and derivatives thereof, kojic acid, chitosan glycolate and salicylate, butylhydroxytoluene, butylhydroxyanisole, nordihydroguaiac resin acid, nordihydroguaiaretic acid, trihydroxybutyrophenone, uric acid and derivatives thereof, mannose and derivatives thereof, selenium and selenium derivatives (e.g. selenium methionine), stilbenes and stilbene derivatives (e.g. stilbene oxide, trans-stilbene oxide). Suitable derivatives (salts, esters, sugars, nucleotides, nucleosides, peptides and lipids) as well as mixtures of these cited active ingredients or plant extracts including these antioxidants can be used according to the invention.

Of this group, tocopherol and derivatives thereof, in particular tocopheryl acetate, and carotinoids as well as butylhydroxytoluene/anisole are preferred as lipophilic, oil-soluble antioxidants.

The total amount of antioxidants in preferred preparations according to the invention is 0.001 to 10 wt. %, preferably 0.05 to 5 wt. % and in particular 0.1 to 2 wt. %, relative to the total preparation.

Complexing substances can also support the deodorizing effect, in that they complex the heavy metal ions (e.g. iron or copper) having an oxidative catalytic effect and render them stable. Suitable complexing agents are selected from the aforementioned complexing agents.

The invention secondly provides a cosmetic product comprising
i) a dispensing device, comprising
    at least one container including a plunger, which serves as a wall for the container and can be moved by means of a dispensing mechanism (in particular a nut-and-spindle arrangement),
    at least one outlet, which is fluidically connected to said container,
ii) a composition of the first subject matter of the invention included in said container.

The composition of the first subject matter of the invention can be discharged from the outlet of the dispensing device by actuating the dispensing mechanism. The plunger is moved and the composition of the first subject matter of the invention is pressed in the direction of the outlet. The pressure that develops as a result forces said composition out of said dispensing device through the at least one outlet.

The present application thirdly provides the non-therapeutic use of the compositions of the first subject matter of the invention to reduce or mask body odor.

The present application fourthly provides a non-therapeutic method for reducing or masking body odor, characterized in that a composition of the first subject matter of the invention is applied to the skin in an effective amount using a suitable applicator. The composition according to the invention more preferably remains on the skin for a period of 1 minute to 24 hours, preferably 2 to 12 hours.

A more preferred embodiment of the invention is characterized by the following points:
1. An anhydrous composition including, relative in each case to the total weight of the composition,
    at least one antiperspirant active ingredient,
    at least one oil in a total amount from 20 to 80 wt. %, at least one fatty alcohol having 12 to 18 carbon atoms,
at least one fatty alcohol having more than 18 carbon atoms,
with the proviso that
the total amount of fatty alcohols is 3 to 12 wt. %,
the weight ratio of fatty alcohols having 12 to 18 carbon atoms to the other
fatty alcohols is in a weight ratio range from 1:1 to 1:3.
2. The anhydrous composition according to point 1, characterized in that the at least one antiperspirant active ingredient is included in an amount from 3 to 35 wt. %, preferably 5 to 30 wt. % and more preferably 10 to 23 wt. %, relative to the total weight of active substance (USP) free from water of crystallization in the total composition.
3. The anhydrous composition according to one of points 1 or 2, characterized in that the oils are included in a total amount from 30 to 80 wt. %, more preferably from 40 to 75 wt. %, particularly preferably from 45 to 70 wt. %.
4. The anhydrous composition according to one of points 1 to 3, characterized in that at least one volatile oil is included as the oil.
5. The anhydrous composition according to point 4, characterized in that at least one volatile silicone oil and/or at least one $C_8$-$C_{16}$ isoparaffin is included as the volatile oil.
6. The anhydrous composition according to one of points 1 to 5, characterized in that the total amount of fatty alcohols is 4 to 9 wt. %.
7. The anhydrous composition according to one of points 1 to 6, characterized in that relative to the total weight thereof the fatty alcohols having 18 carbon atoms are included in a total amount of 2.0 to 5.0 wt. %.
8. The anhydrous composition according to one of points 1 to 7, characterized in that relative to the total weight thereof the fatty alcohols having 20 to 28 carbon atoms are included in a total amount of 0.8 to 2.0 wt. %.
9. The anhydrous composition according to one of points 1 to 8, characterized in that relative to the total weight thereof the fatty alcohols having 30 to 38 carbon atoms are included in a total amount of 0.6 to 1.5 wt. %.
10. The anhydrous composition according to one of points 1 to 9, characterized in that relative to the total weight thereof the fatty alcohols having 40 to 48 carbon atoms are included in a total amount of 0.2 to 0.7 wt. %.
11. The anhydrous composition according to one of points 1 to 10, characterized in that relative to the total weight thereof, less than 0.05 wt. % of fatty alcohols having more than 50 carbon atoms are included.
12. The anhydrous composition according to one of points 1 to 11, characterized in that the weight ratio of fatty alcohols having 12 to 18 carbon atoms to the other fatty alcohols is in a weight ratio range from 1:1 to 1:1.3.
13. The anhydrous composition according to one of points 1 to 12, characterized in that the weight ratio of fatty alcohols having 20 to 28 carbon atoms to fatty alcohols having 30 to 38 carbon atoms is in a weight ratio range from 1:0.5 to 1:2, in particular from 1:0.9 to 1:0.6.
14. The anhydrous composition according to one of points 1 to 13, characterized in that the weight ratio of fatty alcohols having 20 to 28 carbon atoms to fatty alcohols having 40 to 48 carbon atoms is in a weight ratio range from 1:0.1 to 1:1, in particular from 1:0.2 to 1:0.4.
15. The anhydrous composition according to one of points 1 to 14, characterized in that it additionally contains at least one lipophilic thickening agent, in particular of the silicone elastomer type.
16. Non-therapeutic use of a composition according to one of points 1 to 15 to reduce or mask body odor.
17. A non-therapeutic method for reducing or masking body odor, characterized in that a composition according to one of points 1 to 15 is applied to the skin in an effective amount using a suitable applicator.
18. A cosmetic product, comprising
    i) a dispensing device, comprising
        at least one container containing a plunger, which serves as a wall for the container and can be moved by means of a dispensing mechanism (in particular a nut-and-spindle arrangement),
        at least one outlet, which is fluidically connected to said container,
    ii) a composition according to one of points 1 to 15 contained in said container.

The examples below are intended to clarify the invention without restricting its scope thereto. Unless otherwise specified, all stated amounts relate to percentages by weight relative to the total weight of the corresponding composition.

EXAMPLES

The following soft solid compositions were produced:

| Raw material | A | B | C | D | E | F | G |
|---|---|---|---|---|---|---|---|
| Dow Corning 9040 Silicone Elastomer Blend | 5.0 | 5.0 | 5.0 | 5.0 | 5.0 | 5.0 | 5.0 |
| Cyclopentasiloxane | 69.5 | 65.5 | 51.5 | — | 66.5 | 32.75 | 65.5 |
| C10-13 isoparaffin | — | — | — | 51.5 | — | 32.75 | — |
| Aerosil 300[1] | 0.5 | 0.5 | 0.5 | 0.5 | 0.5 | 0.5 | 0.5 |
| Stearyl alcohol | 2.1 | 3.8 | 2.1 | 2.1 | 3.8 | 3.8 | 3.8 |
| Performacol 425 alcohol[2] | 2.9 | 5.2 | 2.9 | 2.9 | 5.2 | 5.2 | 5.2 |
| Dry Flo PC[3] | — | — | 6.5 | 6.5 | — | — | — |
| Talc | — | — | 11.9 | 11.9 | — | — | — |
| Aluminum zirconium pentachlorohydrex gly (AAZG 3110) | 20.0 | 20.0 | 20.0 | 20.0 | — | — | — |
| Aluminum zirconium trichlorohydrex gly (AAZG 531) | — | — | — | — | 23.0 | — | 20.0 |
| Aluminum chlorohydrate (Microdry 3110) | — | — | — | — | — | 20.0 | — |

[1] INCI name: Silica (fumed silica, average particle size: 7 µm, Evonik)
[2] INCI name: C20-40 Alcohols (Baker Petrolite)
[3] INCI name: Aluminum Starch Octenylsuccinate (hydrophobically modified corn starch with a molecular weight of 10,000, AKZO)

The antiperspirant active ingredient was suspended in cyclopentasiloxane with a silicone elastomer and silica. The optional further components Dry Flo PC and talc were likewise suspended. The fatty alcohols were then added while stirring until a thickened soft solid had formed.

The compositions were stable and exhibited no syneresis, even under pressure. The formulations had a light, powdery dry feeling when applied to the skin.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An anhydrous composition comprising, relative in each case to the total weight of the composition,
   at least one antiperspirant active ingredient,
   at least one oil in a total amount from 20 to 80 wt.%,
   at least one fatty alcohol having 12 to 18 carbon atoms,
   at least one fatty alcohol having more than 18 carbon atoms including at least one fatty alcohols having 20 to 28 carbon atoms and fatty alcohols having 30 to 38 carbon atoms in a weight ratio range from 1:0.5 to 1:2,
   with the proviso that
   the total amount of fatty alcohols is 3 to 12 wt.%,
   the weight ratio of fatty alcohols having 12 to 18 carbon atoms to the other fatty alcohols is in a weight ratio range from 1:1 to 1:3.

2. The anhydrous composition according to claim 1, characterized in that the at least one antiperspirant active ingredient is included in an amount from 3 to 35 wt.% relative to the total weight of active substance (USP) free from water of crystallization in the total composition.

3. The anhydrous composition according to claim 1, characterized in that the oils are included in a total amount from 30 to 80 wt.%.

4. The anhydrous composition according to claim 1, characterized in that at least one volatile oil is included as the oil.

5. The anhydrous composition according to claim 4, characterized in that at least one volatile silicone oil and/or at least one $C_8$—$C_{16}$ isoparaffin is included as the volatile oil.

6. The anhydrous composition according to claim 1, characterized in that the total amount of fatty alcohols is 4 to 9 wt.%.

7. The anhydrous composition according to claim 1, characterized in that the weight ratio of fatty alcohols having 12 to 18 carbon atoms to the other fatty alcohols is in a range from 1:1 to 1:1.3.

8. The anhydrous composition according to claim 1 characterized in that the at least one fatty alcohol having more than 18 carbon atoms comprises fatty alcohols having 20 to 28 carbon atoms and fatty alcohols having 40 to 48 carbon atoms in a weight ratio range from 1:0.1 to 1:1.

9. The anhydrous composition according to claim 1, characterized in that the anhydrous compositoin additionally comprises at least one lipophilic thickening agent of the silicone elastomer type.

10. A cosmetic product, comprising
    i) a dispensing device, comprising
       at least one container including a plunger, which serves as a wall for the container and can be moved by means of a dispensing mechanism, and
       at least one outlet, which is fluidically connected to said container; and
    ii) a composition according to claim 1 contained in said container.

11. An anhydrous composition comprising, relative in each case to the total weight of the composition,
    at least one antiperspirant active ingredient,
    at least one oil in a total amount from 20 to 80 wt.%,
    at least one fatty alcohol having 12 to 18 carbon atoms,
    at least one fatty alcohol having more than 18 carbon atoms including at least one fatty alcohols having 20 to 28 carbon atoms and fatty alcohols having 40 to 48 carbon atoms in a weight ratio range from 1:0.1 to 1:1, with the proviso that
    the total amount of fatty alcohols is 3 to 12 wt.%,
    the weight ratio of fatty alcohols having 12 to 18 carbon atoms to the other fatty alcohols is in a weight ratio range from 1:1 to 1:3.

12. The anhydrous composition according to claim 11, characterized in that the at least one antiperspirant active ingredient is included in an amount from 3 to 35 wt.% relative to the total weight of active substance (USP) free from water of crystallization in the total composition.

13. The anhydrous composition according to claim 11, characterized in that the oils are included in a total amount from 30 to 80 wt.%.

14. The anhydrous composition according to claim 11, characterized in that at least one volatile oil is included as the oil.

15. The anhydrous composition according to claim 14, characterized in that at least one volatile silicone oil and/or at least one $C_8$—$C_{16}$ isoparaffin is included as the volatile oil.

16. The anhydrous composition according to claim 11, characterized in that the total amount of fatty alcohols is 4 to 9 wt.%.

17. The anhydrous composition according to claim 11, characterized in that the weight ratio of fatty alcohols having 12 to 18 carbon atoms to the other fatty alcohols is in a range from 1:1 to 1:1.3.

18. The anhydrous composition according to claim 11 characterized in that the at least one fatty alcohol having more than 18 carbon atoms comprises at least one fatty alcohols having 20 to 28 carbon atoms and fatty alcohols having 30 to 38 carbon atoms in a weight ratio range from 1:0.5 to 1:2.

19. The anhydrous composition according to claim 11, characterized in that the anhydrous compositoin additionally comprises at least one lipophilic thickening agent of the silicone elastomer type.

20. A cosmetic product, comprising
    i) a dispensing device, comprising
       at least one container including a plunger, which serves as a wall for the container and can be moved by means of a dispensing mechanism, and
       at least one outlet, which is fluidically connected to said container; and
    ii) a composition according to claim 11 contained in said container.

* * * * *